United States Patent [19]

Peters

[11] 4,007,734
[45] Feb. 15, 1977

[54] BLOOD PRESSURE INDICATOR
[76] Inventor: Rudolph W. Peters, 5786 Balmoral Drive, Oakland, Calif. 94619
[22] Filed: June 2, 1975
[21] Appl. No.: 582,637
[52] U.S. Cl. .............................. 128/2.05 G; 116/70
[51] Int. Cl.² ......................................... A61B 5/02
[58] Field of Search ................. 128/2.05 C, 2.05 G, 128/2.05 M, 2.05 R; 116/65, 70

[56] References Cited
UNITED STATES PATENTS

| | | | |
|---|---|---|---|
| 1,982,505 | 11/1934 | Emerson | 128/2.05 G |
| 3,373,613 | 3/1968 | Whitmore | 128/2.05 G |
| 3,411,476 | 11/1968 | Warren et al. | 116/70 |
| 3,572,208 | 3/1971 | Mott | 116/65 X |
| 3,654,915 | 4/1972 | Sanctuary | 128/2.05 M |
| 3,910,222 | 10/1975 | Metivier | 116/70 |
| 3,929,129 | 12/1975 | Archambault | 128/2.05 C |

Primary Examiner—Kyle L. Howell
Attorney, Agent, or Firm—Harris Zimmerman

[57] ABSTRACT

A blood pressure indicator adapted for self-examination includes a blood pressure arm cuff having an inflatable bladder, and a pair of pressure sensing switches impinging on the bladder and set to audibly or visually indicate the maximum systolic and diastolic pressure permissible. The bladder is inflatable by a flexible bulb connected thereto through a hose and a unidirectional flow valve which maintains inflation of the bladder. As air leaks out of the bladder, the patient notes when the pulse returns to the brachial artery, in relation to the indications given by the switches to ascertain whether the blood pressure falls within the permissible tolerances.

9 Claims, 7 Drawing Figures

U.S. Patent  Feb. 15, 1977  Sheet 1 of 2  4,007,734
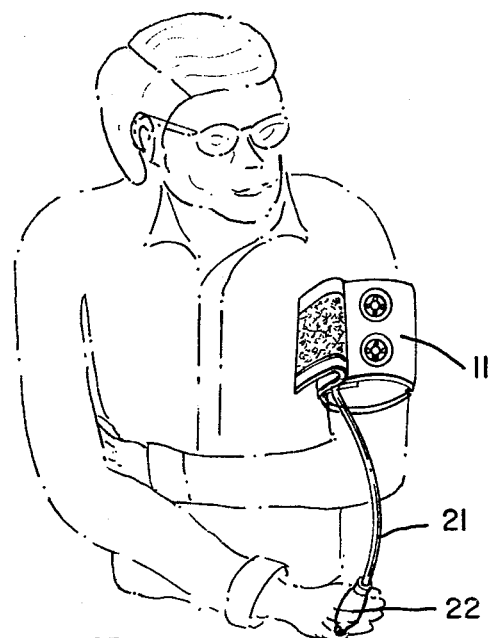
FIG_1
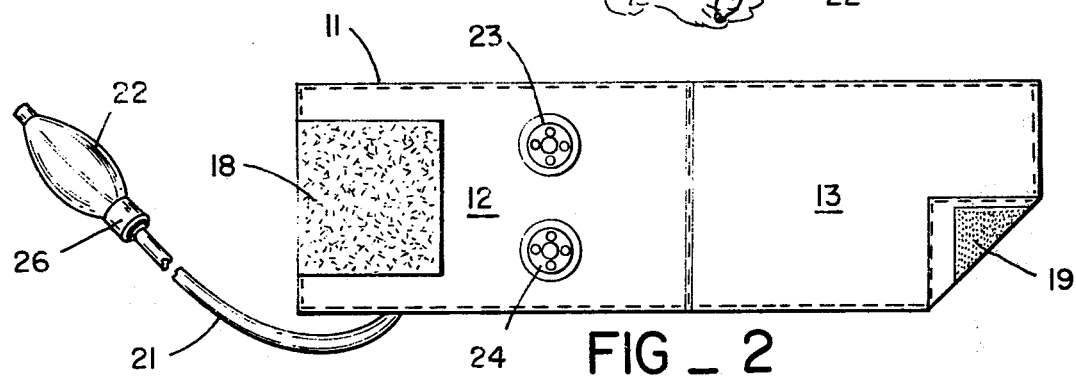
FIG_2
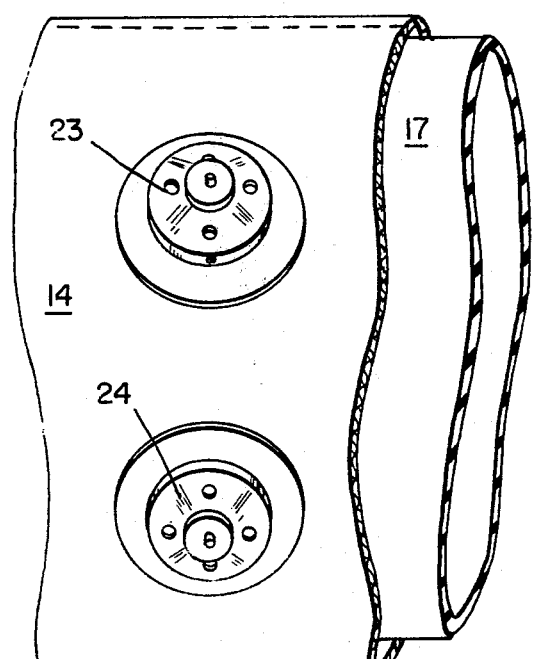
FIG_3
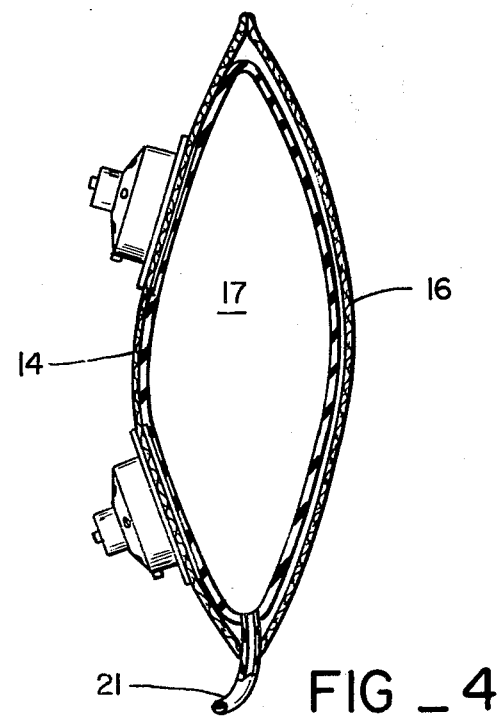
FIG_4

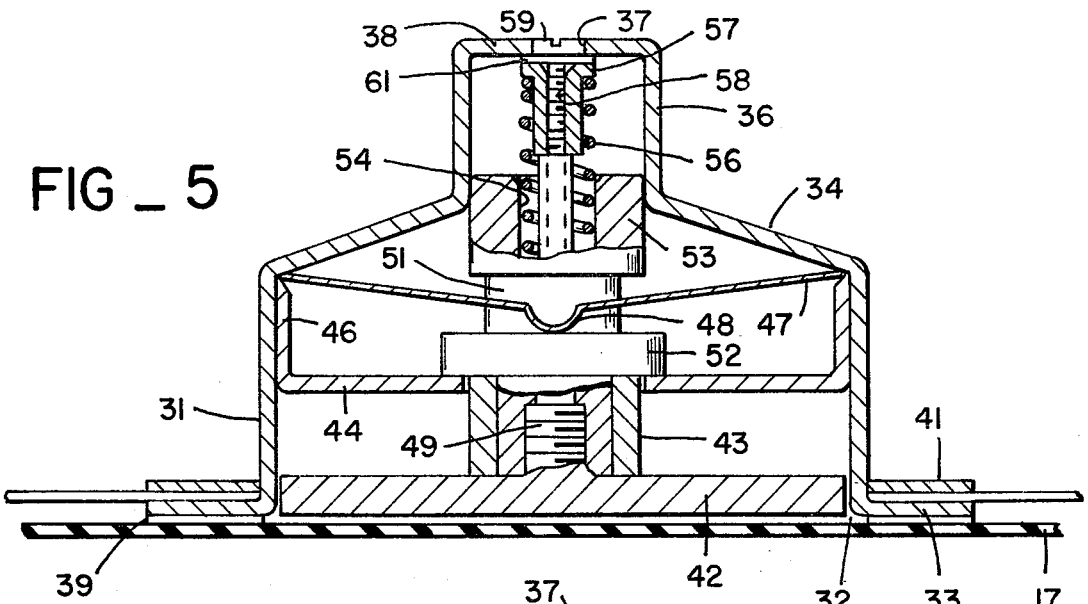
FIG _ 5
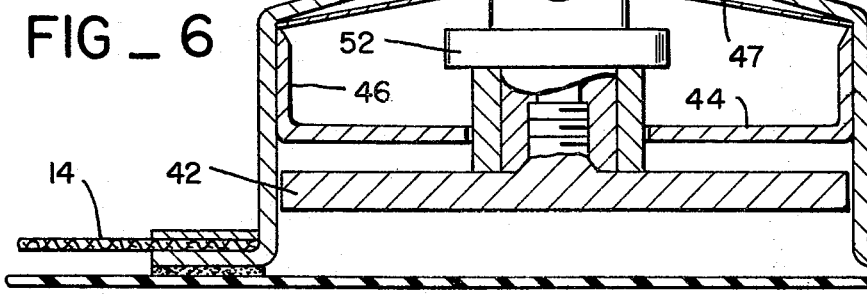
FIG _ 6
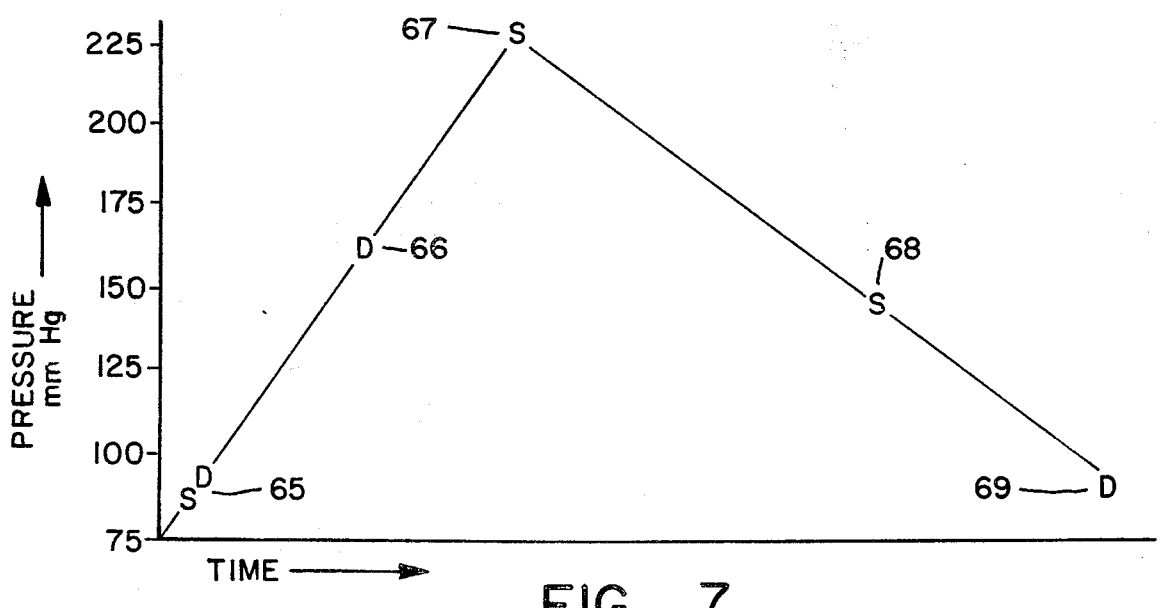
FIG _ 7

BLOOD PRESSURE INDICATOR

BACKGROUND OF THE INVENTION

In recent years medical research has shown a definite correlation between a number of serious ailments and the presence of hypertension in the sufferers of these ailments. It has also become apparent that the onset of hypertension very often precedes these ailments, such as cardio-vascular disease, kidney disease, and the like. Therefor it is vitally important to determine which individuals suffer from hypertension, and to monitor and control their high blood pressure.

For those persons known to suffer from hypertension, an important element in treatment is the periodic and frequent monitoring of their blood pressure to determine the effects of psychological and physiological stress, medication, and the like. This is usually accomplished by requiring the patient to visit frequently a clinic or physician's office to have his/her blood pressure measured. It would be more desirable and convenient for the patient to self-monitor periodically the blood pressure. However, a sphygmomanometer is too elaborate and complex for many individuals to operate with a sufficient degree of reliability.

SUMMARY OF THE INVENTION

The present invention generally comprises a blood pressure indicating device with which an individual may easily determine whether his/her blood pressure falls within predetermined upper and lower limits. It includes a cuff adapted to be wrapped and secured about an arm, an inflatable bladder within the cuff, and a rubber bulb for inflating the bladder through a flexible tube. A unidirectional flow valve in the bulb maintains inflation of the bladder, and a fixed bleed port allows the pressure in the bladder to decrease slowly and smoothly.

Secured to the cuff and impinging on the bladder are a pair of pressure switches. Each pressure switch includes a plunger which is resiliently biased toward the bladder and translatable thereby within a housing. The housing includes an annular over-center spring secured to the plunger which generates an audible click as it translates through the center position. The amount of air bladder pressure required to translate the plunger through the center position is determined by an adjustable spring means also secured to the plunger.

THE DRAWING

FIG. 1 is a depiction of the use of the blood pressure indicator of the present invention.

FIG. 2 is a plan view of the blood pressure indicator of the present invention.

FIG. 3 is an enlarged view of a portion of the cuff of the present invention.

FIG. 4 is a cross-sectional view of the cuff of the present invention.

FIG. 5 is a cross-sectional view of a pressure switch of the present invention, shown in the un-actuated position.

FIG. 6 is a cross-sectional view of a pressure switch of the present invention, shown in the actuated position.

FIG. 7 is a graphical representation of the switch actuation sequence of the present invention.

DESCRIPTION OF THE PREFERRED EMBODIMENT

The present invention generally comprises a blood pressure indicating device which is adapted for use by unskilled medical personnel, or for self-examination. It is designed to indicate quickly, easily, and unambiguously whether or not the blood pressure value falls within limits of acceptable systolic and diastolic pressure. As shown in FIG. 2, it includes a cuff 11, formed of flexible, durable fabric, having opposed ends 12 and 13. The end 12 includes two layers of fabric 14 and 16 joined at their respective edges, with an inflatable air bladder 17 disposed and secured therebetween. Extending from the bladder is a flexible tube 21 joined to an inflating bulb 22. Disposed of fabric layer 14 of end 12 is a fabric fastener 18, such as the hook portion of a hook and loop fastener. The other side of end 13 includes a fabric fastener 19, such as the loop portion counterpart of fastener 18. It may be appreciated that when the cuff is wrapped about a limb such as an arm with the side 16 adjacent to the skin, the fastening portions 18 and 19 are confronting and disposed to join the ends 12 and 13 snugly about the arm.

Also joined to the fabric layer 14 of end 12 of the cuff are a pair of pressure switches 23 and 24, as shown in FIG. 3, impinging on the air bladder 17. Each switch is adapted to generate an audible or visual signal in response to an adjustably set, predetermined pressure exerted thereon by the inflated bladder. One switch is set to signal the maximum diastolic pressure. As shown in FIG. 1, the cuff is wrapped about an arm by the user, and snugly secured with the fabric fasteners. The bladder is then inflated by means of the bulb 22, a unidirectional flow valve 26 joined thereto maintaining the inflation of the bladder as it is pumped up to close the brachial artery, as is well known in the art. When the artery has closed and no pulse is felt, inflation is stopped and a fixed bleed port associated with the valve 26 slowly leaks air to allow the pressure in the bladder to decline gradually and smoothly.

As the bladder air pressure falls the systolic indicating switch is actuated, followed soon thereafter by the diastolic indicating switch. The falling air pressure also permits the brachial artery to open when the blood pressure therein exceeds the external pressure applied by the bladder. At this point the pulse will return to the arm and will be felt by the user of the device. If the pulse returns before the systolic indicating switch is actuated, the blood pressure is higher than the maximum systolic pressure desirable. If the pulse returns after the systolic indicating switch is actuated the blood pressure is less than the maximum systolic parameter.

Likewise, if a pulse is felt in the arm after the diastolic indicating switch is actuated, the diastolic pressure is less than the preset diastolic maximum. If no pulse is felt, the diastolic pressure is too high. Thus an untrained individual may easily monitor his/her blood pressure, using the device of the present invention.

Various forms of adjustable, indicating pressure switches may be employed as switches 23 and 24. One novel form of such a switch is shown in FIGS. 5 and 6. It comprises a cylindrical housing 31 having an open end 32 and a radially outwardly extending flange 33 joined to that end. The housing includes an inwardly extending truncated conical section 34, and an axially aligned cylindrical portion 36 extending therefrom. A hole 37 is axially disposed in the closed end 38 of the portion 36.

The housing extends through a circular hole in the fabric 14, with the flange 33 disposed between the fabric 14 and the air bladder 17. An adhesive ring 39 joins the flange to the surface of the bladder. A locking ring 41 press fit onto the housing is pressed down toward the flange 33 to retain the fabric 14 therebetween and secure the housing in place. Slidably disposed in the open end 32 of the housing is a circular bladder contact plunger 42, which includes a rectangular spacer block 43 joined axially thereto. Disposed within the housing is a circular retainer plate 44 which is provided with a centrally disposed square hole through which the spacer block 43 freely extends. The plate 44 includes a peripheral flange 46 which is press fit into the housing to retain the plate therein.

Disposed within the housing is an over-center spring 47, which comprises a resilient metal disk having a centrally disposed hole therein and a laterally disposed curved channel 48 extending between the hold and the periphery of the spring. The spring is retained between the press fit flange 46 and the internal surface of the conical portion 34 of the housing. Joined to the block 43 by screw means 49 is a spindle 51 which extends freely through the hole in the spring 47. The spindle includes spaced shoulders 52 and 53 between which the spring 47 may freely flex.

The upper shoulder 53 is freely and slidably disposed within the portion 36 of the housing. The shoulder 53 includes a hole 54 extending centrally into the upper end thereof. Received in the hole 54 is a helical spring 56 secured about a spring keeper 57. The spring keeper includes a central, threaded bore 58 which receives an adjustment screw 59 extending therein from the hole 37 in the housing. It may be appreciated that the screw 59 includes a lip 61 impinging on the inner surface of end 38, and rotation of the screw selectively varies the spacing of the spring carrier from end 38 to control the force applied by spring 56 to the spindle.

The force of the inflating bladder on the plunger 42 is initially opposed both by the resilience of spring 47 and by the adjustable spring 56. As the bladder pressure exceeds these combined spring forces the plunger and spindle 51 translate away from the bladder. As the shoulder 52 urges the spring 47 through the center position the spring 47 snaps into impingement with shoulder 53, as shown in FIG. 6, generating a loud clicking sound. This click indicates that an air bladder pressure corresponding to the combined spring forces has been reached.

The air in the bladder is then allowed to exhaust slowly through bleed port in valve 26. The force of spring 56 is now opposed to the force of spring 47. Thus as the bladder contracts the pressure on the plunger at the instant when the spring 47 snaps back onto shoulder and clicks is less than the pressure required to generate the initial click.

The switch actuation sequence is depicted graphically in FIG. 7, the systolic sensing represented by S and the diastolic sensing switch represented by D. With the cuff deflated completely both switches are in their unactuated position, as indicated at 65. As the cuff bladder is inflated the diastolic switch actuates and clicks at a pressure 66, and the systolic switch actuates and clicks at a higher pressure 67. Inflation is stopped and air then begins to leak from the bladder. At pressure 68, which is substantially lower than pressure 67, the systolic switch again clicks, indicating the maximum desirable systolic pressure. At pressure 69 the diastolic switch clicks to indicate the maximum diastolic pressure, also lower than pressure 66.

Thus when using the blood pressure indicator of the present invention which embodies switches according to the embodiment of FIGS. 5 and 6, the user inflates the cuff as described in the foregoing until both switches have clicked (at point 67). The cuff bladder is then allowed to slowly exhaust, and the return and maintenance of the pulse is noted with respect to the clicks indicated at 68 and 69, as described in the foregoing.

It should be emphasized that many forms of pressure indicating switches giving audible or visual signals may be employed in the present invention. Further, although two switches are disclosed in conjunction with the preferred embodiment, any number of switches may be employed, set at staggered indicating pressures to define ranges of desirable blood pressure.

I claim:

1. A device for indicating blood pressure, comprising a cuff adapted to be secured about a limb, said cuff including an inflatable bladder, means for inflating and deflating said bladder, and at least one pressure sensing switch secured to said cuff; said pressure sensing switch including plunger means resiliently biased to impinge on said bladder, and sound emitting means actuated by said plunger means for signalling a predetermined pressure exerted by said bladder on said plunger means and the limb.

2. The device of claim 1, including a pair of pressure sensing switches, said pair including a first pressure sensing switch for indicating a desirable systolic pressure limit, and a second pressure sensing switch for indicating a desirable diastolic pressure limit.

3. The device of claim 1, wherein said plunger means includes a plunger impinging on the exterior surface of said bladder.

4. The device of claim 3, including a housing in which said plunger is translatably disposed, said housing secured to said cuff.

5. The device of claim 4, including adjustable spring means for biasing said plunger toward said bladder.

6. The device of claim 4, said sound emitting means including an over-center spring disposed in said housing and translatable by said plunger to snap through the center position.

7. The device of claim 6, including a spindle extending from said plunger and operatively connected to said over-center spring.

8. The device of claim 1, wherein said inflating means includes a resilient bulb, a tube for connecting said bulb to said bladder, and a unidirectional flow valve disposed between said bulb and said tube.

9. The device of claim 1, wherein said inflating means includes a fixed bleed port for slowly exhausting said bladder.

* * * * *